US010383738B2

(12) United States Patent
O'Connor et al.

(10) Patent No.: US 10,383,738 B2
(45) Date of Patent: Aug. 20, 2019

(54) TIBIAL COMPONENT

(71) Applicant: BTG International Limited, London (GB)

(72) Inventors: John J. O'Connor, Headington (GB); John W. Goodfellow, Oxford (GB); David Murray, Cuddesdon (GB)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 15/259,283

(22) Filed: Sep. 8, 2016

(65) Prior Publication Data
US 2017/0119534 A1    May 4, 2017

Related U.S. Application Data

(63) Continuation of application No. 14/597,885, filed on Jan. 15, 2015, now abandoned, which is a (Continued)

(30) Foreign Application Priority Data

Jun. 16, 1999    (GB) .................................. 9914074.1

(51) Int. Cl.
*A61F 2/38* (2006.01)
*A61F 2/30* (2006.01)

(52) U.S. Cl.
CPC ............ *A61F 2/3868* (2013.01); *A61F 2/389* (2013.01); *A61F 2002/30324* (2013.01);
(Continued)

(58) Field of Classification Search
CPC .......... A61F 2/38; A61F 2/3868; A61F 2/389; A61F 2002/30324; A61F 2002/30326;
(Continued)

(56) References Cited

U.S. PATENT DOCUMENTS

| 4,298,992 A | 11/1981 | Burstein et al. ............... 3/1.911 |
| 4,586,933 A * | 5/1986 | Shoji ..................... A61F 2/3886 |
| | | 623/20.29 |

(Continued)

FOREIGN PATENT DOCUMENTS

| EP | 0 069 683 A | 1/1983 |
| EP | 0 353 921 A | 2/1990 |

(Continued)

*Primary Examiner* — Alvin J Stewart
(74) *Attorney, Agent, or Firm* — Finnegan, Henderson, Farabow, Garrett & Dunner, L.L.P.

(57) ABSTRACT

A tibial knee joint prosthesis for attachment to a suitably prepared tibial bone, providing bearing portions in the lateral and medial compartments. The lateral and medial bearing surfaces of the component are inclined at different angles in the anterior to posterior direction of the knee, so that when mounted to the tibia, the lateral bearing surface of the prosthesis is higher than the medial bearing surface to the posterior side of the knee. In this way the lateral ligament is tightened progressively more than the medial ligament as the knee moves from extension to flexion, resulting in increased stability in the lateral compartment.

2 Claims, 5 Drawing Sheets

Related U.S. Application Data continuation of application No. 13/067,143, filed on May 11, 2011, now abandoned, which is a continuation of application No. 12/461,435, filed on Aug. 11, 2009, now Pat. No. 8,066,776, which is a continuation of application No. 11/407,129, filed on Apr. 20, 2006, now abandoned, which is a continuation of application No. 10/692,016, filed on Oct. 24, 2003, now Pat. No. 7,060,101, which is a continuation of application No. 10/014,920, filed on Dec. 14, 2001, now abandoned, which is a continuation of application No. PCT/GB00/02334, filed on Jun. 16, 2000.

(52) U.S. Cl.
CPC ............ *A61F 2002/30326* (2013.01); *A61F 2002/30629* (2013.01); *A61F 2002/30935* (2013.01)

(58) Field of Classification Search
CPC .. A61F 2002/30629; A61F 2002/30935; A61F 2/4684; A61F 2002/3895; A61F 2002/30751; A61F 2002/30754; A61F 2/30756; A61F 2002/4205; A61F 2/3872
See application file for complete search history.

(56) References Cited

U.S. PATENT DOCUMENTS

| | | | | |
|---|---|---|---|---|
| 4,728,332 A | | 3/1988 | Albrektsson | 623/20.29 |
| 4,808,185 A | * | 2/1989 | Penenberg | A61B 17/1624 623/20.29 |
| 4,936,853 A | | 6/1990 | Fabian et al. | 623/20.15 |
| 4,963,153 A | | 10/1990 | Noseberger et al. | 623/20 |
| 5,047,057 A | * | 9/1991 | Lawes | A61F 2/389 623/20.29 |
| 5,059,216 A | | 10/1991 | Winters | 623/20.32 |
| 5,064,437 A | * | 11/1991 | Stock | A61F 2/3868 623/20.29 |
| 5,192,328 A | | 3/1993 | Winters | 623/20.31 |
| 5,203,807 A | | 4/1993 | Evans et al. | 623/20 |
| 5,219,362 A | | 6/1993 | Tuke et al. | |
| 5,234,433 A | | 8/1993 | Bert et al. | 606/88 |
| 5,275,603 A | | 1/1994 | Ferrante et al. | 606/86 |
| 5,282,870 A | * | 2/1994 | Moser | A61F 2/38 623/20.31 |
| 5,330,533 A | * | 7/1994 | Walker | A61F 2/3868 623/20.31 |
| 5,358,530 A | * | 10/1994 | Hodorek | A61F 2/3868 623/20.29 |
| 5,556,432 A | * | 9/1996 | Kubein-Meesenburg | A61F 2/3868 623/20.21 |
| 5,702,472 A | * | 12/1997 | Huebner | A61F 2/4241 623/21.15 |
| 5,755,802 A | * | 5/1998 | Gerber | A61B 17/1764 623/20.29 |
| 5,824,104 A | | 10/1998 | Tuke | |
| 5,824,105 A | | 10/1998 | Ries et al. | 623/20.31 |
| 5,871,541 A | * | 2/1999 | Gerber | A61F 2/3868 623/20.29 |
| 5,871,542 A | * | 2/1999 | Goodfellow | A61F 2/3868 623/20.16 |
| 5,964,808 A | | 10/1999 | Blaha et al. | 623/20.28 |
| 6,013,103 A | | 1/2000 | Kaufman et al. | 623/20 |
| 6,139,581 A | | 10/2000 | Engh et al. | 623/20.34 |
| 6,190,415 B1 | * | 2/2001 | Cooke | A61F 2/3868 623/20.31 |
| 6,210,443 B1 | | 4/2001 | Marceaux et al. | 623/20.33 |
| 6,235,060 B1 | | 5/2001 | Kubein-Meesenburg et al. | 623/20.31 |
| 6,443,991 B1 | | 9/2002 | Running | 623/20.27 |
| 6,558,427 B2 | | 5/2003 | Leclercq et al. | 623/20.33 |
| 7,060,101 B2 | * | 6/2006 | O'Connor | A61F 2/389 623/20.32 |
| 8,012,216 B2 | * | 9/2011 | Metzger | A61F 2/38 623/20.32 |
| 8,066,776 B2 | * | 11/2011 | O'Connor | A61F 2/3868 623/20.32 |
| 8,075,626 B2 | * | 12/2011 | Dun | A61F 2/3886 623/20.15 |
| 8,246,688 B2 | * | 8/2012 | Hagen | A61F 2/3868 623/14.12 |
| 8,470,048 B2 | * | 6/2013 | Wolfson | A61F 2/3836 623/20.15 |
| 8,858,642 B2 | * | 10/2014 | Metzger | A61F 2/3836 623/20.15 |
| 8,998,993 B2 | * | 4/2015 | Wolfson | A61F 2/3836 623/18.11 |
| 9,060,866 B2 | * | 6/2015 | Fankhauser | A61F 2/38 |
| 9,387,085 B2 | * | 7/2016 | Davignon | A61F 2/389 |
| 2004/0204766 A1 | * | 10/2004 | Siebel | A61F 2/38 623/20.31 |
| 2009/0210066 A1 | | 8/2009 | Jasty | 623/20.31 |

FOREIGN PATENT DOCUMENTS

| | | |
|---|---|---|
| EP | 0 447 652 A | 9/1991 |
| EP | 0 672 397 A | 9/1995 |
| EP | 0 809 987 A | 12/1997 |
| EP | 0 890 347 A | 1/1999 |
| EP | 0 950 387 A | 10/1999 |
| FR | 2 676 916 A | 12/1992 |
| FR | 2 777 452 | 10/1999 |
| GB | 2 138 296 A | 10/1984 |

\* cited by examiner

TIBIAL COMPONENT

CROSS-REFERENCE TO RELATED APPLICATIONS

This application is a continuation of application Ser. No. 14/597,885, filed Jan. 15, 2015 (abandoned) which is a continuation of application Ser. No. 13/067,143, filed May 11, 2011 (abandoned), which is a continuation of application Ser. No. 12/461,435, filed Aug. 11, 2009 (U.S. Pat. No. 8,066,776), which is a continuation of application Ser. No. 11/407,129, filed Apr. 20, 2006 (abandoned), which is a continuation of application Ser. No. 10/692,016, filed Oct. 24, 2003 (U.S. Pat. No. 7,060,101), which is a continuation of application Ser. No. 10/014,920, filed Dec. 14, 2001 (abandoned), which is a continuation of PCT/GB00/02334, filed Jun. 16, 2000, which claims priority to British Patent Application No. 9914074.1, filed Jun. 16, 1999, the entire contents of each of which are hereby incorporated by reference.

The invention relates in general to prosthetic knee joint devices, and in particular to bi-compartmental devices for use in the lateral and medial compartments of the tibia.

BACKGROUND OF THE INVENTION

Considerable development has taken place in recent decades with regard to knee joint replacement. However, continuous review of clinical experience with unicompartmental meniscal knee implants has shown that problems can occur, particularly in the case of replacement of the lateral compartment. Whilst great success has been achieved with medial compartmental replacement, dislocation of the meniscal bearing in the lateral compartment remains a problem. The success rate of such replacements has been limited, due to the fact that the lateral soft tissues (principally the lateral collateral ligament and the ilio-tibial band) offer less certain resistance to distraction of the joint. There is also evidence to suggest that the lateral compartment may lift off under certain circumstances, such as during single leg stance, resulting in unequal loading of the joint. The lateral collateral ligament is a much slimmer structure than the medial collateral ligament and there is evidence to suggest that it is slack in the unloaded joint, except at extension. It therefore offers much less resistance to bearing dislocation or lift-off than do the more inextensible medial structures. On the lateral side, the tendon of the popliteus muscle passes across the postero-lateral corner of the joint. When the joint is replaced, the tendon can act to propel the meniscal bearing towards the intercondylar region where dislocation can occur.

The early total condylar prostheses designed in the 1970's sacrificed both cruciate ligaments as does their successor, the Insall-Burstein posterior stabilised prosthesis. Many of the prostheses designed in the 1980's sacrificed the anterior cruciate ligament (ACL) but allowed retention of the posterior cruciate ligament. Attempts to develop total joint prostheses where the ACL is also retained have generally been unsuccessful. The prosthetic components were either designed to constrain antero-posterior translational movements and inadequate steps were taken to prevent loosening, or the components were unconstrained relative to anterior/posterior translation and many wore out.

It has been observed that during flexion and extension of the knee joint, the contact points between the femoral and tibial condyles move in an antero-posterior direction. The femoral component moves on the tibial plateau in a posterior direction during flexion and in an anterior direction during extension. One of the problems caused by absence of the ACL is increased antero-posterior movement of the femoral condyle relative to the tibial condyle, which is responsible for further loosening of the tibial component and often leads to dislocation. A conventional tibial component will generally have a large central pin for location in the prepared end of the tibia. The ACL may be present in a diseased knee but is usually removed to improve access to the joint area during surgery, which is necessary to provide sufficient clearance to insert the tibial component and provide a site for the central pin.

Examination of records of the state of the ligaments at the time of knee-replacement surgery shows that in more than 50% of cases, both in osteoarthritis or in rheumatoid arthritis, all the ligaments, including the ACL, were found to be intact. Where present, these ligaments are generally sacrificed in the above surgical techniques. Although tibial components having a central cut-out slot of the type illustrated in FIG. 1, which can be inserted with the ACL in place, have been employed, there will still be a tendency for dislocation or lift-off in the lateral compartment.

In those cases where the ligaments are already absent, they may be reconstructed. Since the attempts of the 1960's, the practice of ACL reconstruction in young athletes, using muscle tendons as grafts, has become widespread and there is a large body of surgeons for whom this operation forms a substantial part of their practice. Although such routine reconstructions have usually only been performed in young persons, following injury involving ligament damage, there is considerable scope for reconstruction in the elderly patients who are the usual candidates for knee replacement, in cases where the ACL is absent.

From the foregoing it is apparent that a need exists for knee replacement prostheses which provide sufficient stability in the lateral compartment and which are suitable for joints with intact cruciate ligaments.

SUMMARY OF THE INVENTION

The aim of the invention is to provide a tibial component that will cause the lateral ligament to be tightened relatively more than the medial. It is intended that such a component be suitable in surgical situations where the anterior cruciate ligament is retained, replaced or reconstructed.

In accordance with the present invention, there is provided a prosthesis for implantation in the knee joint, said prosthesis comprising: a tibial component having a first, upper surface and a second, lower surface opposite said first surface for attachment to the tibia, said first surface including a lateral bearing region and a medial bearing region, wherein the respective angles of inclination of said lateral and said medial bearing regions of said first surface, with respect to said second surface, are dissimilar.

Advantageously, the direction of inclination is between the anterior side and the posterior side, and the angle of inclination of the lateral bearing region is more positive than the angle of inclination of the medial bearing region. Preferably, the difference in angle of inclination is approximately 2 to 4 degrees. The angle of the lateral bearing region may be inclined positively to the second surface and the medial bearing region substantially parallel to the second surface. Alternatively, with appropriate changes made to the angles of saw cut in the tibia, the lateral bearing region may be substantially parallel to the second surface, and the medial bearing region inclined at a negative angle to said second surface, or the lateral bearing region can be inclined at a greater positive angle to the second surface, and the medial bearing region inclined at a lesser positive angle to said second surface. The bearing regions may be formed as flat plane plateaux. For added stability, the bearing regions may be given a convex, part-spherical or part cylindrical form. They can also be formed with a convex lateral bearing region and a concave medial bearing region, similar to the physiological knee, or alternatively with either the lateral region convex and the medial region flat, or the lateral region flat and the medial region concave. In practical terms, the angles of inclination of said lateral and said medial bearing regions may be chosen such that, when attached to the tibia, the lateral bearing region is inclined downwards at a lesser angle to the horizontal than the medial bearing region, in an anterior to posterior direction.

There is further provided a method of implanting a prosthesis comprising sawing the medial and lateral compartments of the tibial bone condyles and attaching the prosthesis to the prepared surface of the tibial bone, wherein the angle of the saw cut is chosen such that the posterior side of the lateral bearing region sits higher on the tibia than the posterior side of the medial bearing region.

In an alternative aspect of the invention there is provided a prosthesis for implantation in the knee, said prosthesis comprising: a tibial component for attachment to the tibia, having a first, upper surface and a second, lower surface opposite said first surface for attachment to the tibia, said first surface including a lateral bearing region and a medial bearing region, arranged such that the respective angles of inclination in sagittal planes of said lateral and said medial bearing regions of the component in situ are different.

Preferably the lateral and medial bearing regions are inclined downward, the angle of downward inclination of said lateral bearing region to the horizontal being less than the angle of inclination of said medial bearing region, such that the posterior of the lateral bearing region is higher than the posterior of the medial bearing region.

In a further aspect, the invention provides a prosthesis comprising a tibial component having lateral and medial portions of differing height, wherein the difference in height of the lateral and medial portions increases posteriorly, such as to progressively tighten the lateral ligament more than the medial ligament as the joint moves from extension to flexion.

The complete prosthesis may further comprise intermediate meniscal bearing components and a femoral component for attachment to the femur.

According to another aspect of the invention, there is provided a tibial component having lateral and medial bearing portions and dimensioned such that a difference in the respective thicknesses of the lateral bearing portion and the medial bearing portion increases in an anterior to posterior direction.

A further aspect of the invention provides a tibial component having lateral and medial bearing portions, wherein the thickness of at least one bearing portion changes progressively from the anterior side to the posterior side.

Preferably the cross-sectional area of the lateral bearing portion in a sagittal plane that bisects the lateral bearing portion is greater than the cross-sectional area of the medial bearing portion in a corresponding sagittal plane. The change in thickness of the lateral and medial bearing portions in the anterior to posterior direction is advantageously described by the following expression:

$$t_{lat(p)} - t_{lat(a)} > t_{med(p)} - t_{med(a)}$$

Where $t_{lat(p)}$ is the thickness of the lateral bearing portion to the posterior side, $t_{lat(a)}$ is the thickness of the lateral bearing portion to the anterior side, $t_{med(p)}$ is the thickness of the medial bearing portion to the posterior side and $t_{med(a)}$ is the thickness of the medial bearing portion to the anterior side. A further aspect of the invention provides a tibial component having a lateral and a medial bearing portion comprising means for tensioning the lateral ligaments progressively more than the medial ligament.

BRIEF DESCRIPTION OF THE DRAWINGS

To better illustrate the invention, it will now be described, by way of example, with reference to the accompanying drawings, in which.

DETAILED DESCRIPTION OF PREFERRED EMBODIMENTS

The invention will be described in terms conventionally used to describe the geometry of the knee. The knee has an anterior side (A) and posterior side (P), and is divided laterally along sagittal planes (S) extending between the anterior and posterior sides. A central sagittal plane divides the knee into medial and lateral compartments. The tibia has a vertical, major axis $T_M$ along its length, and a horizontal plane TN defined normal to its major axis. In the figures, (A) denotes the anterior side of the tibial component, (P) denotes the posterior side, (M) denotes the medial side, (L) denotes the lateral side, (S) denotes a sagittal plane, $T_M$ denotes the vertical axis of the tibia, and TN the horizontal plane of the tibia.

Figure 1A:
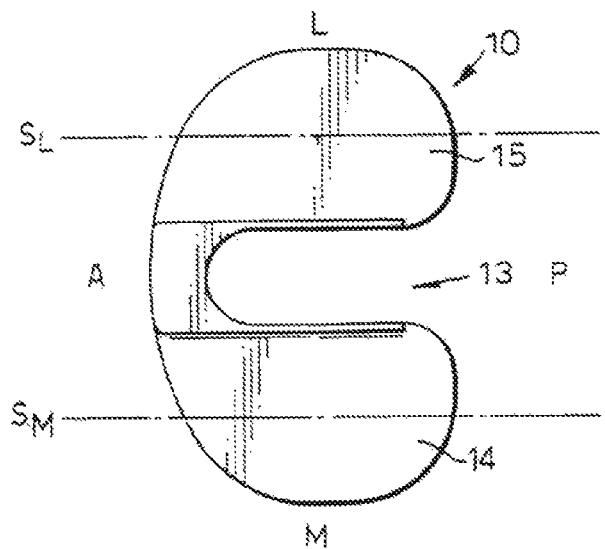
FIGS. 1A, 1B and 1C illustrate a prior art tibial tray component in plan (1aA), side (1B) and posterior (1C) views.
Figure 1B:
Figure 1C:
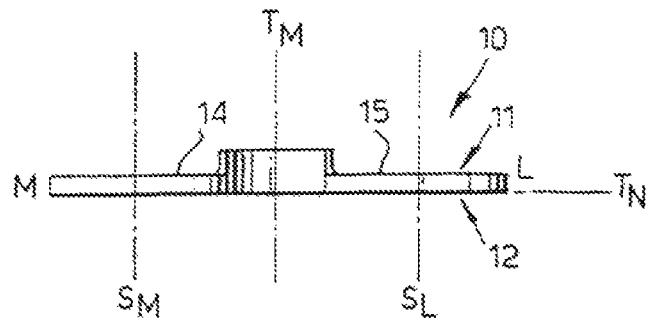

Referring to FIG. 1, the prior art tibial component 10 comprises a generally flat tray, shaped to correspond to the cross-sectional shape of the top of a typically prepared tibial bone, having an anterior side (A), a posterior side (P), and medial and lateral sides (M) and (L). $S_L$ and $S_M$ designate typical sagittal planes, in this case bisecting the lateral and medial bearing portions. The component has a first, upper, major surface 11, which acts as a bearing articulation surface, and a second, lower, major surface 12, opposite the first surface, for attachment to the tibia. A central cutout 13, open at the posterior side (P) of the component, is provided to allow the tray to be slid into position onto a suitably prepared tibia, without being hindered by the presence of the cruciate ligaments. To either side of the central cutout are defined lateral and medial bearing portions having flat meniscal bearing regions 14, 15 parallel to the lower surface 12. The thickness of the component (height of upper surface relative to lower surface) is constant across both bearing regions.

The tibia is typically prepared by sawing the top of the tibia in each compartment at an angle of 7.5° sloping downwards from the horizontal, relative to the front of the tibia. A saw guide is pinned to the exposed bone of the proximal tibia and rests on a shoe around the ankle at the distal end. The slope of the guiding surface is set at an angle of 7.5° to this guide. This guide is used to remove a sliver of bone from the top of the tibia. The tibial component is then attached to the prepared end of the tibia oriented with its cutout facing posteriorly.

With this arrangement, since the surfaces of the lateral and medial bearing regions are parallel to one another, the lateral collateral ligament is insufficiently constrained. A prosthesis with this arrangement will have a tendency to dislocate or lift off.

The inventors have established by 3d digitisation and modelling of the healthy knee joint that the articulating surfaces of the medial and lateral condyles of the tibia are not parallel. The medial tibial condyle of the healthy knee joint is slightly concave while the lateral condyle is slightly convex. Study of the digitised shapes of cadaver specimens has enabled the positions of planar surfaces which best fit the two condyles to be determined. A representative analysis of knee joints shows that on average, in the sagittal plane, the angle of posterior inclination (i.e. in an anterior to posterior direction) of the best-fit plane to the medial tibial condyle relative to the normal axis of the tibia is around 2 degrees greater than the angle of posterior inclination for the lateral tibial condyle, in other words, the upper surface of the medial condyle of the tibia slopes downward from front to back at an angle on average 2 degrees greater than the upper surface of the lateral condyle.

Basing their ideas on this realisation, the inventors have developed an improved prosthetic component, which takes into account the difference in posterior inclination between the lateral and medial condyles.

Figure 2A:
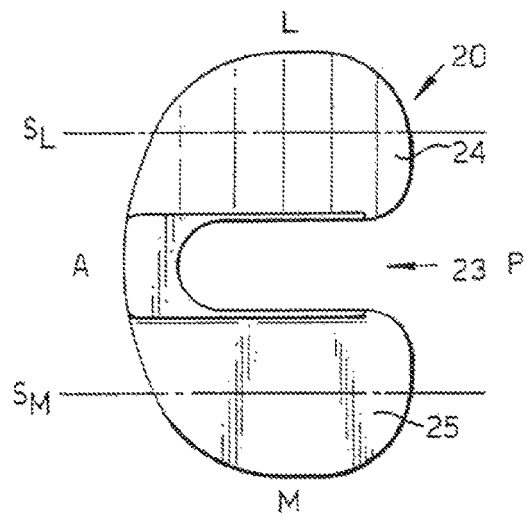
FIGS. 2A, 2B and 2C depict plan, side and posterior views of a tibial component according to a first embodiment of the invention, for incorporation in a right-hand joint.
Figure 2B:
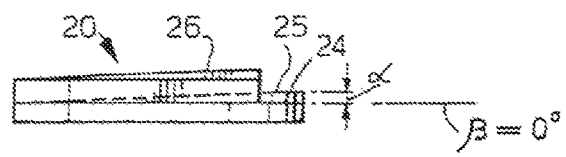
Figure 2C:
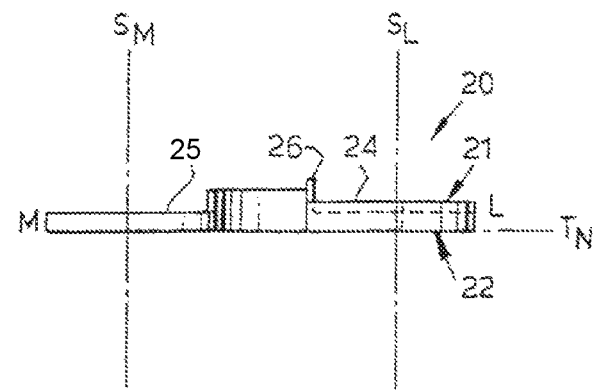
Figure 3A:
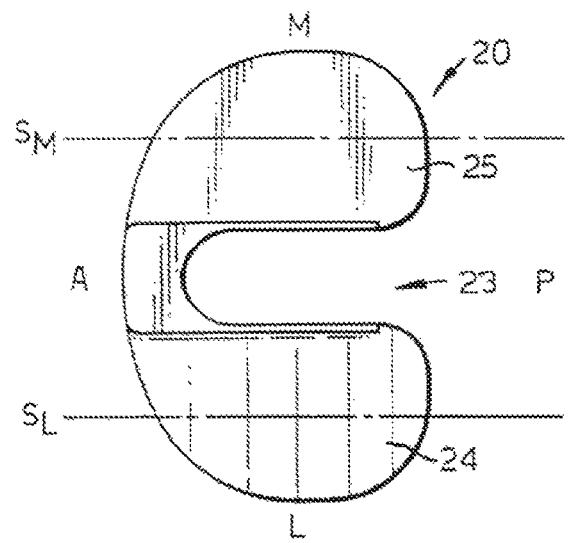
FIGS. 3A, 3B, and 3C depict plan, side and posterior views of a tibial component according to a first embodiment of the invention, for incorporation in a left-hand joint.
Figure 3B:
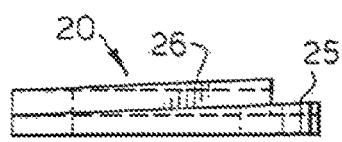
Figure 3C:
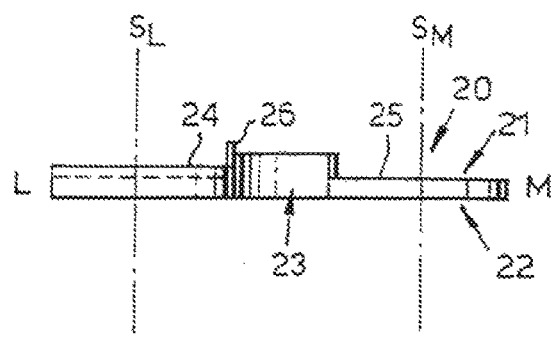
Figure 4A:
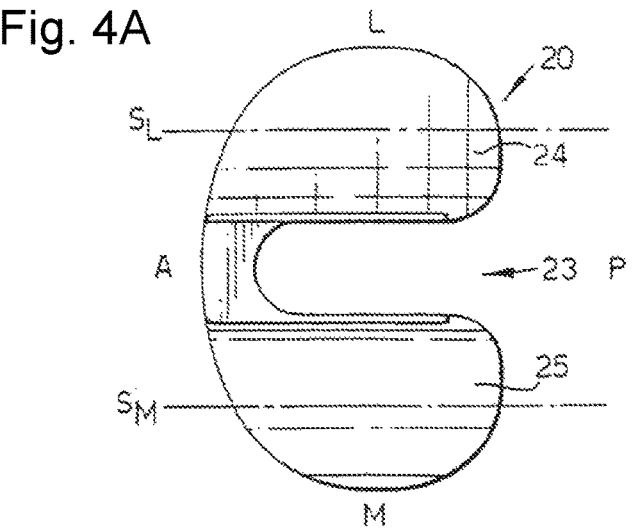
FIGS. 4A, 4B, 4C and 4D depict plan, side and posterior views of a tibial component according to a second embodiment of the invention, for incorporation in a right-hand joint.
Figure 4B:
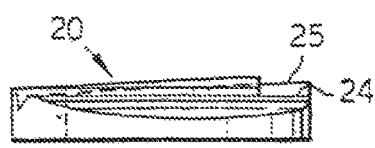
Figure 4C:
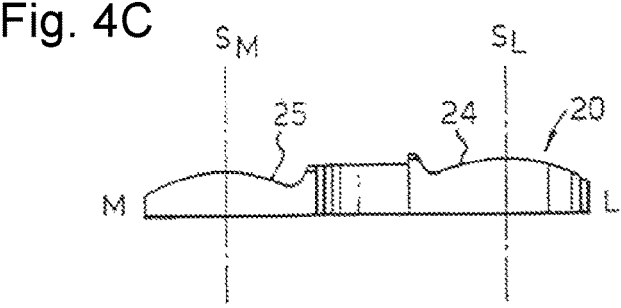
Figure 4D:
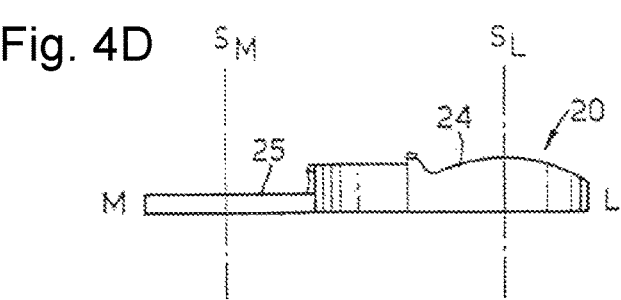

FIGS. 2 and 3 illustrate right and left versions of a bicompartmental tibial tray component 20 in accordance with a first embodiment of the invention, similar to the conventional tibial tray component illustrated in FIG. 1. The component also has a first, upper, major surface 21, which acts as a bearing articulation surface, and a second, lower, major surface 22, opposite the first surface, for attachment to the tibia (not shown). By adjusting the angle of inclination in the sagittal plane of the lateral and medial bearing regions (24,25) to be different, the behaviour of the prosthetic knee joint can be arranged to reduce the likelihood of dislocation in the lateral compartment.

FIGS. 2 and 3 show the plateaux (24, 25) as flat surfaces inclined to each other. In surgery, a single saw guide is used to saw the surfaces of the lateral and medial compartments of the tibia parallel to each other, preferably at an angle of approximately 7.5° to the horizontal plane, normal to the major axis of the tibia. The articulating bearing surface of the component in the medial compartment is inclined at an angle $\beta=0$ i.e. is parallel to its under surface, so will also be inclined at an angle of 7.5°, when mounted to the prepared tibia. The articulating bearing surface in the lateral compartment of the component is inclined at an angle $\alpha$, in the region of 3.5° to its lower surface, the component increasing in thickness in the antero-posterior direction. Thus when the component is mounted to the prepared tibia sawn at 7.5° to the horizontal it will provide a lateral bearing surface inclined at the lesser angle of 4° to the horizontal plane, and consequently the height difference between the medial and lateral bearing surfaces increases posteriorly. This will tend to keep the fibres of the lateral collateral ligament tighter than physiological as the joint flexes and the femoral condyles move backwards, increasing the contribution of the LCL to resisting bearing dislocation or lateral lift-off.

Although the relative inclination in the sagittal plane of the two bearing surfaces with the component in situ will most probably be in the region of 2 to 4 degrees, the essential element is an appropriate difference in slope between the bearing surfaces of the two compartments when the component is in situ, such that the height of the bearing surface on the lateral side reduces progressively at a lesser rate in the posterior direction than the height reduces on the medial side.

In FIGS. 2 and 3, the two plateaux are shown at the same level anteriorly and therefore at different levels posteriorly. The invention encompasses designs in which the lateral and medial bearing surfaces are at different levels both anteriorly and posteriorly; it may be appropriate to arrange the component such that both lateral and medial bearing regions are inclined relative to the lower surface of the component, but at different angles, as will be discussed later in this specification.

It may be appropriate to provide the tibial component with a raised side wall or flange at one side of the intercondylar cutout, as indicated at 26 in FIG. 2, in order to limit the extent of relative lateral/medial movement of the joint and to prevent contact between the meniscal bearings or femoral condyles and the exposed cut tibial bone.

FIG. 4 (*a*) to (*c*) shows a second embodiment of the invention incorporating a component (20) for a profiled meniscal bearing to provide added stability. In this embodiment, by making the bearing surfaces of convex, curved form, the resistance to dislocation can be further enhanced. The tibial plateaux are inclined to each other in the sagittal plane as in FIG. 2, such that, in situ, a plane fitted to the surface of the bearing region in the lateral compartment (24) will be inclined at a lesser angle to the horizontal than in the medial compartment (25). The curved bearing regions (24, 25) shown are defined by convex surfaces of part-cylindrical shape. The surfaces can also be defined by convex surfaces of part-spherical shape. As shown in FIG. 4 (*d*), if only one compartment is provided with a curved surface, advantageously, less bone removal may be required. The medial bearing region can be flat, with the lateral bearing region convex as shown in FIG. 4 (*d*), or alternatively, the lateral bearing region can be flat and the medial bearing region concave. It is also envisaged that bearing surfaces could be formed to more closely approximate the physiological tibial condyles, with the lateral bearing region having a convex form, and the medial bearing region having a concave form. Further improvements to stability may be provided by differentially inclining the surfaces in the frontal plane, such that each bearing region slopes downwards from the centre of the knee towards the exterior of the knee.

The radius of curvature of the cylindrical bearing surface is a function of the size of the prosthesis, and will increase for components destined for a larger knee. However, it is important that the radius be kept within limits, to keep the overall thickness of the tibial component as thin as possible, thus minimising the amount of tibial bone that has to be removed to accommodate the component.

Figure 5:
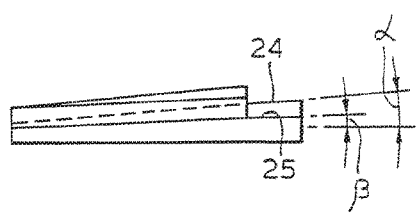
FIG. 5 shows a side view of a tibial component according to a variant of the second embodiment, for incorporation in a right-hand joint.
Figure 6:
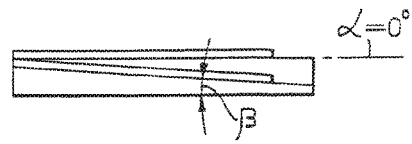
FIG. 6 shows a side view of a tibial component according to an alternative variant of the second embodiment, for incorporation in a right-hand joint.

It is to be appreciated that the actual angles of the articulating bearing surfaces of the tibial component are dependent on the angle of the saw cut in the tibia. A cut angle of 7.5° posterior tilt has been found to be ideal, especially where the femoral component is formed with spherical condyles, allowing the creation of equal flexion and extension gaps. However, the tibial bone could be sawn at other angles, provided that the relative change in thickness of the component in the posterior direction was greater in the lateral compartment than in the medial compartment, with the angles of inclination of the upper surfaces of the component correspondingly selected to achieve the desired differential inclination, when the component is in situ on the tibia. FIG. 5 illustrates a possible variant to the first embodiment. The bearing regions have different slopes but are inclined in the same direction, with the lateral bearing region inclined at 5½° to the lower surface and the medial bearing region inclined at a lesser angle of 2°. Provided the tibial saw cut is made at an increased angle of 9½° the resulting position of the lateral and medial bearing regions in situ on the tibia will be the same as for the first embodiment. It is to be appreciated that with a reduced angle of cut, in order to produce the necessary differential inclination, the component could even have a lateral bearing portion where the upper and lower surfaces were parallel, and a medial bearing portion where the upper surface was inclined in an anterior direction, as illustrated in FIG. 6, where lateral and medial bearing regions have angles of inclination α, β of 0° and −3½° (a negative angle indicating that the bearing region slopes toward the lower surface from the anterior side to the posterior side—as opposed to a positive angle where the bearing region slopes away from the lower surface from the anterior to the posterior side). In this case, a reduced angle of cut of 4° would be necessary to achieve the same overall differential inclination as in the first embodiment. It would also be possible to saw the tibial condyles at different angles, with the lateral compartment inclined at a lesser angle than the medial one, although this would necessitate a more complicated sawing arrangement. In this case a component with parallel medial and lateral plateaux could be employed, having a deformable central section, such that the lower surface of the component could conform to the differentially inclined tibial compartments, once affixed to the tibia. Where appropriate, separate lateral and medial bearing components could be employed.

Figure 7:
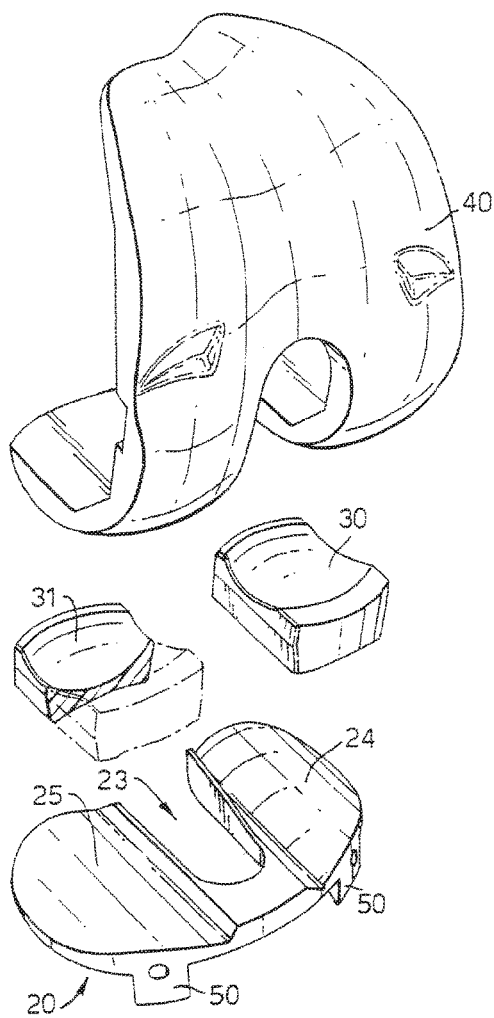
FIG. 7 shows a perspective view of a left-hand total knee prosthesis, incorporating a tibial component according to the second embodiment of the invention.

FIG. 7 shows a complete left-hand 4-part knee prosthesis incorporating the tibial component of the second embodiment. The lateral (24) and medial (25) bearing regions of the tibial component are intended to co-operate in use with the lower bearing surfaces of the intermediate meniscal bearings (30,31). The upper bearing surfaces of the meniscal bearings cooperate in use with the bearing surfaces of a corresponding femoral component (40). As the joint moves from extension to flexion, the femoral component and meniscal bearings will move backwards on the bearing surfaces of the tibial component. Due to the differential inclination of the lateral and medial bearing surfaces, the lateral ligament will be progressively tightened, providing increasing resistance to dislocation as the knee is flexed.

Whilst FIGS. 1 to 6 do not show the means for fixing the tibial component to the bone, it is to be appreciated that this could be achieved in a number of ways. For example, a pin or pins could be applied centrally at the anterior side of the prosthesis, sloping downwards and backwards into the bone. Alternatively, pins or spikes could be applied laterally, as shown at (50) in FIG. 7. Such pins could either be formed as an integral part of the prosthesis, or as separate elements. Slots may be prepared in the tibia to accept the fixing means.

The component may be formed of any suitable surgically acceptable material, such as cobalt chrome vanadium, alumina or zirconia ceramic, or plastic, such as ultra-high molecular weight polyethylene (UHMWPE). Whilst the component described in the above embodiments is of unitary construction it is to be appreciated that it could also be constructed with separate lateral and medial bearing portions secured to one side of a tray element, with the other side of the tray element for attachment to the end of the tibia. Although the above embodiments have generally been described in the context of 3 component total knee prostheses, it is to be appreciated that the invention may also be applied with two component arrangements, where the femoral and tibial components bear directly against one another. In such arrangements, having a lateral tibial plateau which is higher posteriorly could prove particularly useful in reducing any problems of lift-off in extension of the joint. The tibial component in such arrangements may be formed from separate elements, as mentioned above, with bearing portions of a suitable material (e.g. UHMWPE) attached to a metal tray element. The differential inclination may be provided by adapting the tray or the individual bearing portions.

The invention claimed is:

1. A prosthesis for implantation in the knee, said prosthesis comprising: a tibial component for attachment to the tibia, having a first, upper surface and a second, lower surface opposite said first surface for attachment to the tibia, said first surface including a lateral bearing region and a medial bearing region, arranged such that the respective angles of inclination in sagittal planes of said lateral and said medial bearing regions of the component in situ when fitted to the tibia are different,
   wherein the lateral and medial bearing regions in situ are inclined downward to the horizontal from the anterior to the posterior side, the angle of downward inclination of said lateral bearing region to the horizontal being less than the angle of downward inclination of said medial bearing region, such that the posterior of the lateral bearing region is higher than the posterior of the medial bearing region.

2. A tibial component having lateral and medial bearing portions, each of the lateral and medial bearing portions comprising an anterior end and a posterior end, wherein at least one of the bearing portions has a thickness which changes progressively from the anterior end to the posterior end, and wherein the cross-sectional area of the lateral bearing portion in a sagittal plane that bisects the lateral bearing portion is greater than the cross-sectional area of the medial bearing portion in a corresponding sagittal plane, wherein the change in thickness of the lateral and medial bearing portions in the anterior to posterior direction is described by the following expression:

$$t_{lat(p)} - t_{lat(a)} > t_{med(p)} - t_{med(p)} - t_{med(a)}$$

Where $t_{lat(p)}$ is the posterior end thickness of the lateral bearing portion, $t_{lat(a)}$ is the anterior end thickness of the lateral bearing portion, $t_{med(p)}$ is the posterior end thickness of the medial bearing portion and $t_{med(a)}$ is the anterior end thickness of the medial bearing portion.

* * * * *